(12) United States Patent
Schumann et al.

(10) Patent No.: US 9,772,482 B2
(45) Date of Patent: Sep. 26, 2017

(54) ILLUMINATION DEVICE

(71) Applicant: LEICA MICROSYSTEMS CMS GMBH, Wetzlar (DE)

(72) Inventors: Christian Schumann, Giessen (DE); Ralf Krueger, Butzbach Griedel (DE); Tobias Bauer, Koenigstein (DE); Arnold Mueller-Rentz, Brechen (DE); Klaus Hermanns, Asslar (DE); Christian Schulz, Solms (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 0 days.

(21) Appl. No.: 14/437,508

(22) PCT Filed: Oct. 22, 2013

(86) PCT No.: PCT/EP2013/072073
§ 371 (c)(1),
(2) Date: Apr. 22, 2015

(87) PCT Pub. No.: WO2014/064106
PCT Pub. Date: May 1, 2014

(65) Prior Publication Data
US 2015/0293339 A1    Oct. 15, 2015

(30) Foreign Application Priority Data

Oct. 22, 2012  (DE) .................. 10 2012 219 237
Oct. 22, 2012  (DE) .................. 10 2012 219 239

(51) Int. Cl.
*G02B 21/06* (2006.01)
*G02B 21/08* (2006.01)
(Continued)

(52) U.S. Cl.
CPC .......... *G02B 21/06* (2013.01); *F21V 33/0068* (2013.01); *G01N 21/31* (2013.01);
(Continued)

(58) Field of Classification Search
None
See application file for complete search history.

(56) References Cited

U.S. PATENT DOCUMENTS 4,852,985 A    8/1989 Fujihara et al.
6,369,939 B1   4/2002 Weiss et al.
(Continued)

FOREIGN PATENT DOCUMENTS

DE    3734691 A1    4/1988
DE    19845603 A1   5/2000
(Continued)

OTHER PUBLICATIONS

English Machine Translation of the description of WO 2010/052174, Westphal et al., pp. 1-5.*

*Primary Examiner* — Derek S Chapel
(74) *Attorney, Agent, or Firm* — Leydig, Voit & Mayer, Ltd.

(57) ABSTRACT

An illumination device for an optical device, a microscope or a macroscope includes a first illumination source configured to emit light which is directed via an illumination beam path onto an object to be illuminated that is arranged in an object plane. At least one second illumination source is positionable in the illumination beam path, and is transparent or semitransparent as well as self-luminous. The at least one second illumination source is configured to allow light emitted from the first illumination source to pass through at least in part. The object plane having the object to be illuminated is configured to be illuminated both by the first and by the at least one second illumination source.

12 Claims, 9 Drawing Sheets

(51) Int. Cl.
  *G02B 21/18*    (2006.01)
  *F21V 33/00*    (2006.01)
  *G01N 21/31*    (2006.01)
  *F21Y 103/00*   (2016.01)
  *F21Y 105/00*   (2016.01)
  *F21Y 115/20*   (2016.01)
  *F21Y 115/15*   (2016.01)

(52) U.S. Cl.
  CPC ........... *G02B 21/088* (2013.01); *G02B 21/18* (2013.01); *F21Y 2103/00* (2013.01); *F21Y 2105/00* (2013.01); *F21Y 2115/15* (2016.08); *F21Y 2115/20* (2016.08); *G01N 2201/061* (2013.01); *G01N 2201/0628* (2013.01)

(56) References Cited

U.S. PATENT DOCUMENTS

| | | |
|---|---|---|
| 2003/0011910 A1 | 1/2003 | Weiss |
| 2004/0090671 A1 | 5/2004 | Gilbert |
| 2006/0291031 A1 | 12/2006 | Boehm et al. |
| 2007/0211460 A1 | 9/2007 | Ravkin |
| 2007/0297049 A1 | 12/2007 | Schadwinkel et al. |
| 2009/0109525 A1 | 4/2009 | Yamawaki |

FOREIGN PATENT DOCUMENTS

| | | |
|---|---|---|
| DE | 10132360 C1 | 11/2002 |
| DE | 10352040 A1 | 7/2005 |
| DE | 102005036397 A1 | 2/2007 |
| EP | 1416308 A1 | 5/2004 |
| JP | 2001338502 A | 12/2001 |
| JP | 2005245539 A | 9/2005 |
| WO | WO 0005606 A2 | 2/2000 |
| WO | WO 2010052174 A1 | 5/2010 |

\* cited by examiner

ILLUMINATION DEVICE

CROSS-REFERENCE TO PRIOR APPLICATIONS

This application is a U.S. National Stage Application under 35 U.S.C. §371 of International Application No. PCT/EP2013/072073 filed on Oct. 22, 2013, and claims benefit to German Patent Application Nos. DE 10 2012 219 237.9 filed on Oct. 22, 2012 and DE 10 2012 219 239.5 filed on Oct. 22, 2012. The International Application was published in German on May 1, 2014 as WO 2014/064106 A1 under PCT Article 21(2).

FIELD

The present invention relates to an illumination device of an optical device, microscope or macroscope, wherein light emitted from a first illumination source is directed via an illumination beam path onto an object to be illuminated that is arranged in an object plane.

BACKGROUND

In optical devices, for example light microscopes or light macroscopes, in which an object to be investigated is illuminated by a light source, it is generally desirable if the brightness of the light source is modifiable so that the illumination conditions can be optimally adapted to the kind of object to be investigated and to the observation method being used (e.g. bright field, polarization, interference contrast, or phase contrast). Light sources used here are preferably incandescent lamps or halogen lamps, since they are obtainable from numerous manufacturers in a wide variety of configurations in terms of output, operating voltage, filament shape, service life, and color temperature.

On the other hand, a defined and uniform color impression is of crucial importance for routine evaluation of microscope images with high throughput. In pathology, for example, the diagnosis is based to a crucial extent on the color impression of microscopic images of tissue sections. In comparison microscopy and comparison macroscopy, an identically colored presentation is indispensable in order for the comparison task to be performed reliably.

A variety of methods exist for modifying or adjusting the color impression in microscopy. On the one hand, for example, for observation through eyepieces and with the use of arc lamps for illumination, the applied lamp current can be increased in order to modify the color temperature. This is disadvantageous, however, in that the service life of the lamp decreases. An associated increase in brightness, which for certain applications can be desired, may need to be compensated for, for example by means of neutral density filters, for other applications in which the color impression of an object is to be modified.

Spectral emission is furthermore constrained by physical laws (Planck's radiation law), so that the spectral distribution of the intensity is modifiable only within specific limits. Increasing the lamp current is also energy-inefficient.

When a camera image is used, it is possible to perform a white balance at the camera. Cameras that are competitive with the human eye in terms of sensitivity in the context of high-throughput analysis of pathology samples are, however, costly. In addition, a camera image and a subsequent check must be carried out, which can critically slow down the workflow.

It is known to introduce variable colored filters into the illumination beam path, both to furnish a color-neutral illumination at different brightnesses, and to modify the color impression. An approach of this kind is proposed, for example, in DE 101 32 360 C1. The furnishing of such filters proves, however, to be costly in terms of manufacture and relatively coarse when establishing a desired color-neutral brightness setting or a desired change in color impression.

It is also known to use particular prism arrangements in the imaging beam path; this procedure is also to be regarded as complex and costly. In comparison microscopy and comparison macroscopy, bifurcated glass fibers are sometimes used in the illumination beam path so that the light of an illumination source can be used to illuminate both observed objects. Bifurcated glass fibers of this kind are, however, complicated to manufacture and correspondingly costly.

When illuminating microscopic samples and imaging them with objectives having a low magnification and large field of view, the problem furthermore often arises that illumination of the sample is not homogeneous or constant, in particular that it decreases toward the edge of the field of view, so that the overall optical impression is inhomogeneous. In the case of a decreasing illumination intensity toward the edge of the field of view, what results, for example, is a correspondingly darker optical impression at the edge of the field of view. The reason for this is the emission characteristic of conventionally available light sources. The light sources preferably used are in turn the incandescent lamps or halogen lamps mentioned above.

The available concepts for correcting inhomogeneous illumination of the field of view are limited conventionally to neutral density filters that are introduced into the respective illumination beams. Neutral density filters of this kind are considered disadvantageous in that they are not modifiable in terms of the distribution of optical density over the field of view. Flexible adaptation to different inhomogeneous illumination situations is thus as a rule not possible with a neutral density filter. It further proves to be disadvantageous that the full luminous intensity of the light source cannot be used, since homogenization requires that a portion of the light be reflected or absorbed. A radial homogenization filter embodied in this fashion is known, for example, from WO 0005606.

In order to adapt the illumination to different objectives it is usual, especially when objectives having a large field of view are used, to furnish by design a second illumination optical system for lower magnifications, as well as a changing mechanism.

This situation proves disadvantageous in particular with incident illumination systems, since here the object represents a component of the illumination optical system. When multiple objectives are furnished, for example on an objective turret, it is thus necessary for provide for each objective a neutral density filter, as well as a changing mechanism that must be synchronized with the objective turret. Approaches of this kind are inflexible and require considerable design outlay. Approaches of this kind are moreover not sustainable for all the relevant parameters, among which may be mentioned here, for example, objective changing, numerical aperture changing, contrast methods, or also centering and focusing within the illumination system, e.g. adjusting, centering, and focusing the field diaphragm.

It is furthermore known, when digital imaging by means of a camera is used, to perform a subsequent digital illumination correction called a "shading correction." The contrast of a camera image is determined, however, by way of the illumination intensity and the predefined dynamic range of the camera. In many applications it is therefore not possible to compensate by means of a shading correction for a loss of contrast due to poor or inhomogeneous illumination. A shading correction of this kind is furthermore, as already mentioned, usable only when a digital camera is utilized. This method is not available for direct observation of an object through an eyepiece.

SUMMARY

In an embodiment, the present invention provides an illumination device for an optical device, a microscope or a macroscope. A first illumination source is configured to emit light which is directed via an illumination beam path onto an object to be illuminated that is arranged in an object plane. At least one second illumination source is positionable in the illumination beam path, and is transparent or semitransparent as well as self-luminous. The at least one second illumination source is configured to allow light emitted from the first illumination source to pass through at least in part. The object plane having the object to be illuminated is configured to be illuminated both by the first and by the at least one second illumination source.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
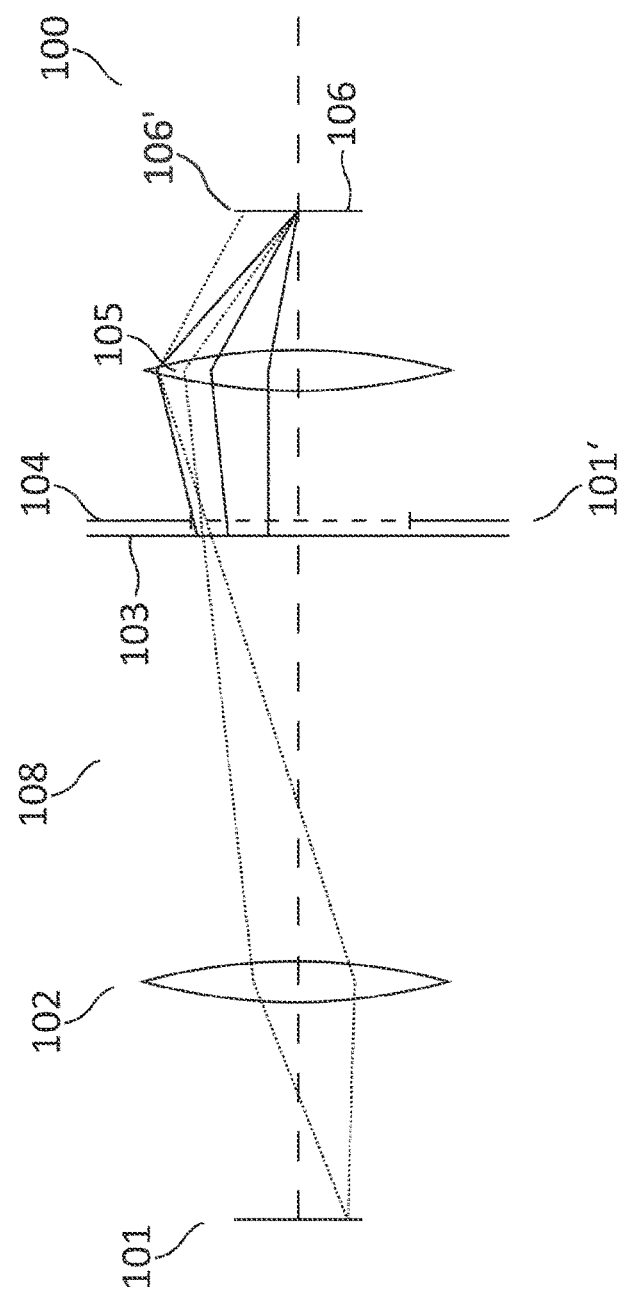
FIG. 1 is a schematic side view of a first preferred embodiment of an illumination device according to the present invention.

In an embodiment, the present invention provides a flexibly adjustable illumination device for optical devices with which, depending on requirements, modification of a color impression or also a color-neutral brightness adjustment and/or homogeneous illumination of a field of view, is possible in simple fashion.

In an embodiment, the invention makes available a very energy-efficient and economical capability for controlling the color and/or brightness of illumination light. Variable color filters, which are both costly to acquire and also energy-inefficient as a result of absorption properties, can in particular be omitted. According to an embodiment of the present invention, illumination light can, for example, be adjusted very accurately to a "desired" color impression or a desired frequency spectrum. Homogenization of an illumination field can also be furnished in simple fashion.

Embodiment of the second illumination source as a self-luminous layer is particularly preferred.

According to a first preferred embodiment, the at least one transparent or semi-transparent self-luminous layer positionable in the illumination beam path is embodied as an electroluminescent layer. Light-emitting diodes and electroluminescent films may be recited as examples of such electroluminescent layers.

It is particularly preferred that the self-luminous layer be embodied as an OLED or as a TOLED. "OLED" or "organic light-emitting diode" is the term for luminous thin-layer components made of organic semiconducting materials. They differ from inorganic light-emitting diodes (LEDs) in terms of practical utilization in that their current density and luminance are lower. In addition, single-crystal materials are not necessary. OLEDs are made of an organic layer sequence whose total thickness can be approximately 200 nm. This layer sequence is introduced between an anode and a cathode. The substrate used is usually glass onto which a transparent conductive layer, e.g. indium tin oxide (ITO), is applied as a cathode. That is followed by the organic layer sequence, and then a, for example, metallic cathode. If the cathode, or a driver electrode that is used, is also transparent, the term "transparent OLED" or "TOLED" is used. The organic materials are applied either by evaporative deposition at 300° to 400°, or in liquid form. OLED layers or TOLED layers can easily be arranged to lie above or behind one another so that, for example, when OLEDs or TOLEDs having different frequency spectra are used, color components corresponding to the frequency spectrum of a respective OLED can be blended in desired fashion into the illumination light of a conventional light source. For example, three OLEDs or TOLEDs arranged above one another, which together extend over or parameterize a suitable color space, e.g. an RGB color space, can be used.

It is further preferred that the at least one second illumination source or self-luminous layer be embodied in the aperture plane of the illumination beam path or in the vicinity of the aperture plane or in an intermediate image plane or in the vicinity of the intermediate image plane. With this feature, homogeneous color correction over the entire field of view can be made available in a particularly effective fashion.

The transparency (or semitransparency) of the arrangement furthermore ensures complete or considerable transmission of the illumination light of the first light source or main light source. Because of the shallow depth of field of microscope illumination systems in the intermediate image plane, it is easily possible to embody a self-luminous layer by superimposition of emitters differing in terms of color, in particular corresponding OLED layers or TOLED layers.

It is particularly preferred that the at least one self-luminous layer be embodied in an intermediate image plane of a KOhler illumination beam path, or in the vicinity of such an intermediate image.

The result of arranging the at least one self-luminous layer in the intermediate image plane is that the luminous pattern of the self-luminous area is imaged onto the object surface or sample surface.

Be it noted, however, that it is also possible for the at least one second illumination source or self-luminous layer to be arranged at other positions or planes of the illumination beam path.

According to a further preferred embodiment, the at least one self-luminous layer is embodied as a flat or curved surface, such that the layer can be applied in particular onto the surface of an optical element, for example a lens or a curved mirror, that is provided in the illumination beam path.

The result of the illumination, provided according to an embodiment of the present invention, of an object plane or of an object with two illumination sources, the second of which is transparent or semitransparent to the light of the first illumination source, is that a desired manipulation or adaptation of the illumination light for an object to be observed can be furnished in a particularly simple and effective manner. In particular, an inhomogeneous illumination by a first light source can effectively be compensated for by corresponding activation of the second light source. The color temperature of the illumination light as a whole can also, for example, be adjusted by means of the second light source.

A very energy-efficient and economical capability for planarly patterned variable control of the illumination light is made available thanks to the preferred use of locally or individually activatable regions of the self-luminous transparent or semitransparent layer or layers (i.e. layers having a number of individually activatable regions, i.e. at least two individually activatable regions). Position-dependent illumination correction of a field of view can thereby be furnished in simple fashion. It is possible in particular to dispense with neutral density filters, which are both costly to furnish and have low energy efficiency as a result of absorption properties. A very homogeneous field of view for different microscope or macroscope settings can thus be furnished.

Usefully, the apparatus according to an embodiment of the present invention comprises a device which provides individual electrical activation of the individual regions of the at least one self-luminous layer. When multiple layers are provided, and with corresponding individual electrical activation of the individual layers, it is possible to modify the intensity of the blended-in color components by corresponding application of the electrical activation, and thereby to adjust the color impression of the illumination light.

For example, it is possible to embody the respective self-luminous layers in three-dimensionally or planarly patterned fashion, and to furnish selective electrical activation of the individual regions. With selective activation of this kind, individual regions of the area can be furnished to have different luminous intensities. This is achieved in particular by means of suitable contacting apparatuses and a corresponding electronic activation system (control unit). By means of flexible activation of this kind, further light can be blended, selectively with position-dependent patterning and brightness, into the illumination light of, for example, a conventional light source, e.g. an LED or filament.

When multiple self-luminous layers having different frequency spectra and corresponding individual electrical activation of the individual layers are provided, it is furthermore possible to modify the intensity of the blended-in color components by corresponding metering of the electrical activation, and thus to adjust the color impression of the illumination light, in particular to keep it constant for different intensities.

The three-dimensional pattern can in particular exhibit a rotational symmetry around the optical axis of the illumination optical system. It can also be made up, however, for example of individual rectangular pixels or segmented regions, in particular quadrilaterals, rectangles, squares, or circles.

According to a preferred embodiment of the microscope or macroscope according to the present invention, the latter is embodied as a comparison microscope or comparison macroscope having at least two sub-microscopes or image channels, at least one sub-microscope or image channel, or all the sub-microscopes or image channels, being embodied with an illumination device according to an embodiment of the present invention, in particular for controlling the color or brightness of illumination light. Comparison microscopes or comparison macroscopes of this kind are utilized, for example, in forensics. With an embodiment of the present invention, for example, production variations that occur in nominally identical light sources can be compensated for in simple fashion and with no intensity loss.

FIGS. 1 to 5 show a preferred embodiment of the invention that is configured for color temperature compensation. FIGS. 6 to 10 show a preferred embodiment of the invention that is set up in particular for homogeneity compensation.

The preferred embodiment depicted in FIG. 1 of an illumination device having an apparatus for controlling the color of illumination light is labeled 100 in its entirety, and serves to illuminate an object 106 positioned in an object plane 106'. The illumination device can be embodied, for example, for a microscope or macroscope.

Illumination device 100 comprises a light source 101, for example in the form of an incandescent lamp or LED, the light of which is guided via a system of lenses 102, 105 along an illumination beam path 108 in order to illuminate object 106 that is to be investigated.

Lens 102 is embodied as a collector lens, and lens 105 as a condenser lens. It is of course possible to provide, at the positions of these lenses, collector or condenser optical systems each encompassing multiple lenses.

An aperture diaphragm 104, by means of which the illumination light intensity can be regulated, is embodied in a plane 101 conjugated with the plane of light source 101.

At least one semitransparent, self-luminous layer 103, which preferably is embodied as an OLED, is introduced into illumination beam path 108 in this conjugated plane 101' (aperture plane) or close to said plane.

The spectral composition of the illumination light as a whole, and thus the color impression of the object, is controllable by controlling or adjusting the intensity and/or frequency spectrum of this at least one self-luminous layer 103, the light of which is directed onto object 106 together with the illumination light of light source 101.

The arrangement depicted in FIG. 1, having an aperture diaphragm and the at least one self-luminous layer in the conjugated plane of the light source, represents globally a KOhler illumination with which very homogeneous color correction can be made available over the entire field of view.

It is also possible, however, to arrange the at least one self-luminous layer in a different plane. In particular, the at least one self-luminous layer 103 can be applied, for example, onto one of lenses 102, 105, or a lens of the corresponding collector or condenser optical system.

Preferably two or three individually activatable semi-transparent layers 103 arranged above one another, for example OLED layers or TOLED layers, are provided. The shallow depth of field of the pupil image of microscope illumination systems ensures imaging into the same object plane on object 106.

Figure 2:
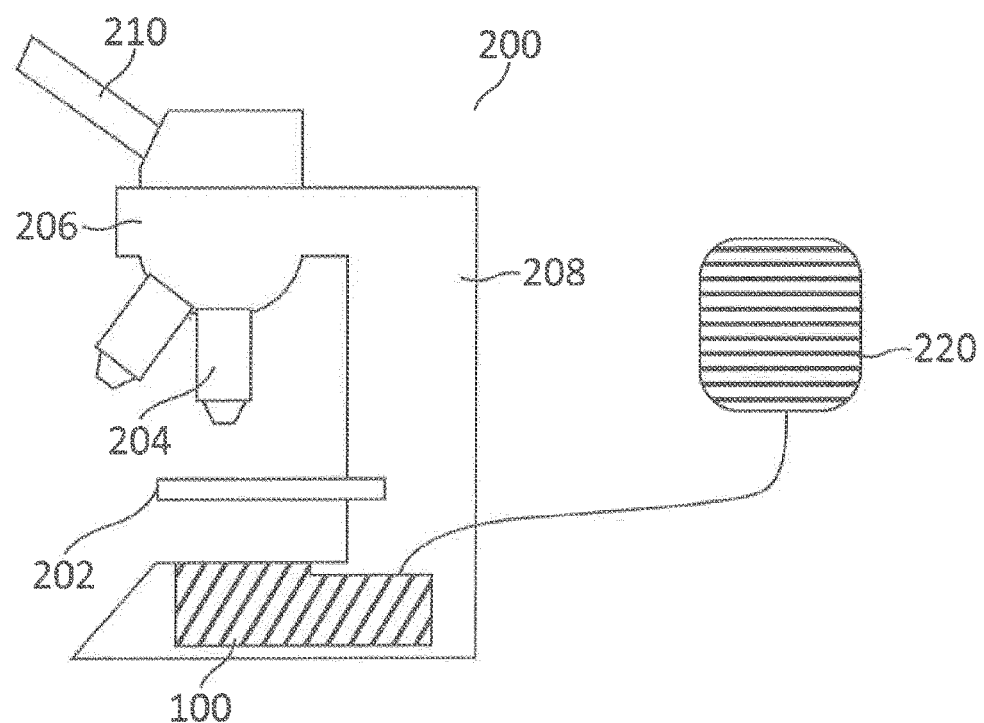
FIG. 2 is a schematic view of a first preferred embodiment of a microscope embodied with an illumination device according to the present invention.

In FIG. 2 a first preferred embodiment of a microscope embodied with an illumination device according to the present invention is labeled 200 in its entirety. When a "microscope" is referred to hereinafter, i.e. with reference to FIGS. 2 to 5, the term "macroscope" is also always to be encompassed thereby as well. Microscope 200 is embodied with a transmitted illumination device 100 that comprises, for example, corresponding components 101, 102, 103, 104, 105 for transmitted illumination of an object positionable on a specimen slide 202. Further components of microscope 200 are likewise depicted merely schematically in FIG. 2. Multiple objectives or magnification optics 204 provided on an objective turret 206, a microscope housing 208, and an eyepiece 210 are, for example, apparent.

The frequency spectrum and/or the brightness, and thus the color impression, of the illumination light furnished by illumination device 200 is controllable by means of a control unit 220. If illumination device 100 encompasses, for example, three OLED layers or TOLED layers (103), as described above with reference to FIG. 1, these are individually activatable with regard to their brightness or intensity so that desired color components can be blended into the illumination light from (main) light source 101. As mentioned, production variations in light sources can thereby be compensated for in simple fashion.

Figure 3:
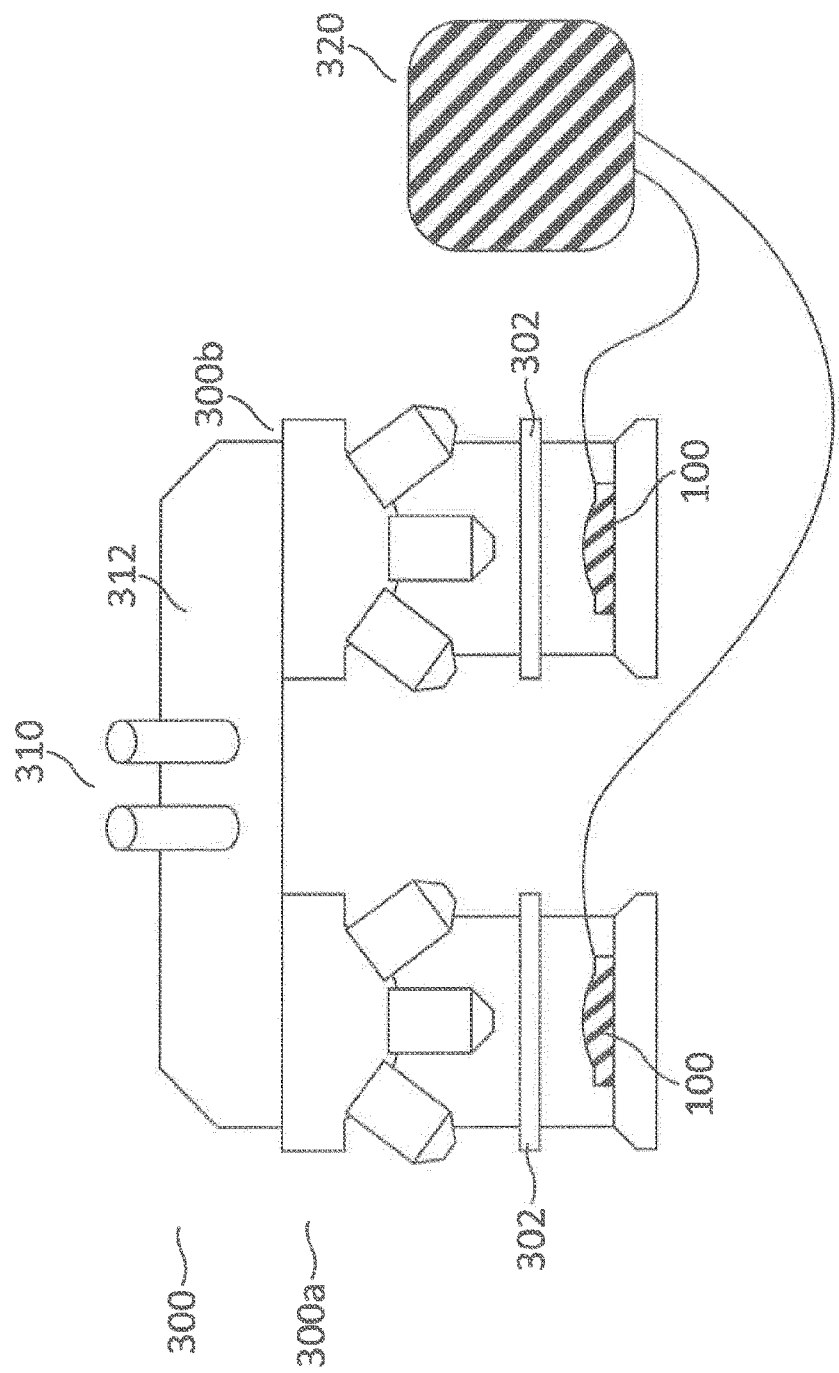
FIG. 3 is a schematic view of a first preferred embodiment of a comparison microscope embodied with an illumination device according to the present invention.

In FIG. 3 a further preferred embodiment of a microscope that is embodied with an illumination device according to the present invention is labeled 300 in its entirety. Microscope 399 is embodied as a comparison microscope that serves for simultaneous observation or analysis of different samples. Comparison microscope 300 comprises two sub-microscopes 300a, 300b that are connected to one another via an optical bridge 312. The two image channels that can thereby be furnished allow a split field of view, which can be observed through one eyepiece or two eyepieces 310, to be furnished.

Each of sub-microscopes 300a, 300b is embodied with an illumination device 100 according to an embodiment of the present invention. Devices 100 are individually controllable by means of a control device 320 in the manner already described.

In comparison microscopy it is essential, for optimum comparison of two samples that are being imaged via sub-microscopes 300a, 300b, that the illumination conditions, i.e. the illumination impression, of the two sub-microscopes match exactly. A corresponding color compensation can be carried out, for example, by introducing a reference sample into the respective sub-microscopes. In the case of the transmitted illumination depicted, for example, in FIG. 3, transparent samples that are placed onto the respective specimen stages 302 are suitable for this. Be it noted that in the case of a comparison microscope having incident illumination, homogeneous diffusion samples are used for this purpose.

By observation of the two image channels furnished by the two sub-microscopes through eyepiece 310, it is possible to mix in the color components, for example in accordance with a suitable parameterization, by corresponding activation of the respective OLED layers or TOLED layers. For example, it is useful to use three TOLED layers or OLED layers with which an RGB (red-green-blue) parameterization can be carried out. The frequency spectrum, and thus the color impression, of the two illumination apparatuses can thereby be optimally adapted or adjusted to one another.

As mentioned, in comparison microscopes or comparison macroscopes this adjustment capability can be provided separately for each image channel. In accordance with simpler embodiments, it is also possible to embody only one of the two image channels or one of the two sub-microscopes 300a, 300b with an illumination device of this kind having the capability for controlling the color of illumination light.

Figure 4:
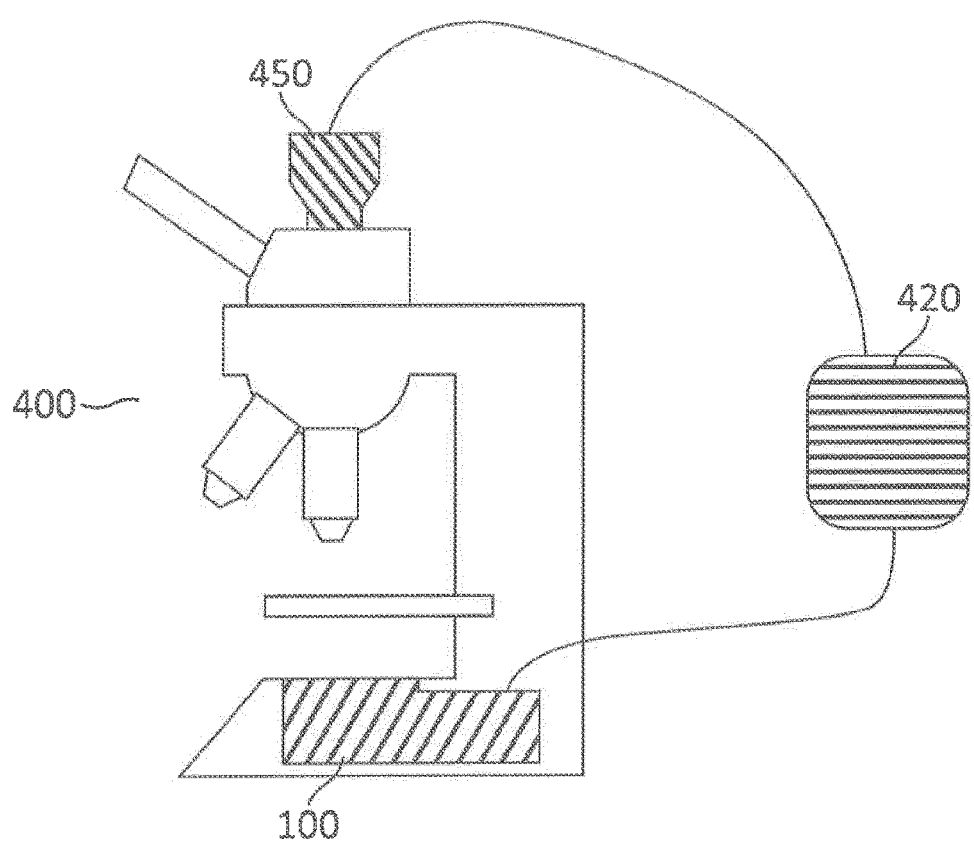
FIG. 4 is a schematic view of a second preferred embodiment of a microscope embodied with an illumination device according to the present invention.

A further preferred embodiment of a microscope having an illumination device according to the present invention is depicted in FIG. 4 and labeled 400 in its entirety. The microscope depicted in FIG. 4 corresponds to the one depicted in FIG. 2, a digital camera 450 additionally being provided. It is possible by means of such a camera, using an illumination device 400 according to the present invention, to establish an automatic adjustment of the frequency spectrum or color impression of the illumination device. This color correction can be accomplished, for example, by means of the control unit here labeled 420, with the aid of an automatic algorithm. The latter can, for example, regulate detected color values of a reference sample to a previously defined target value.

Figure 5:
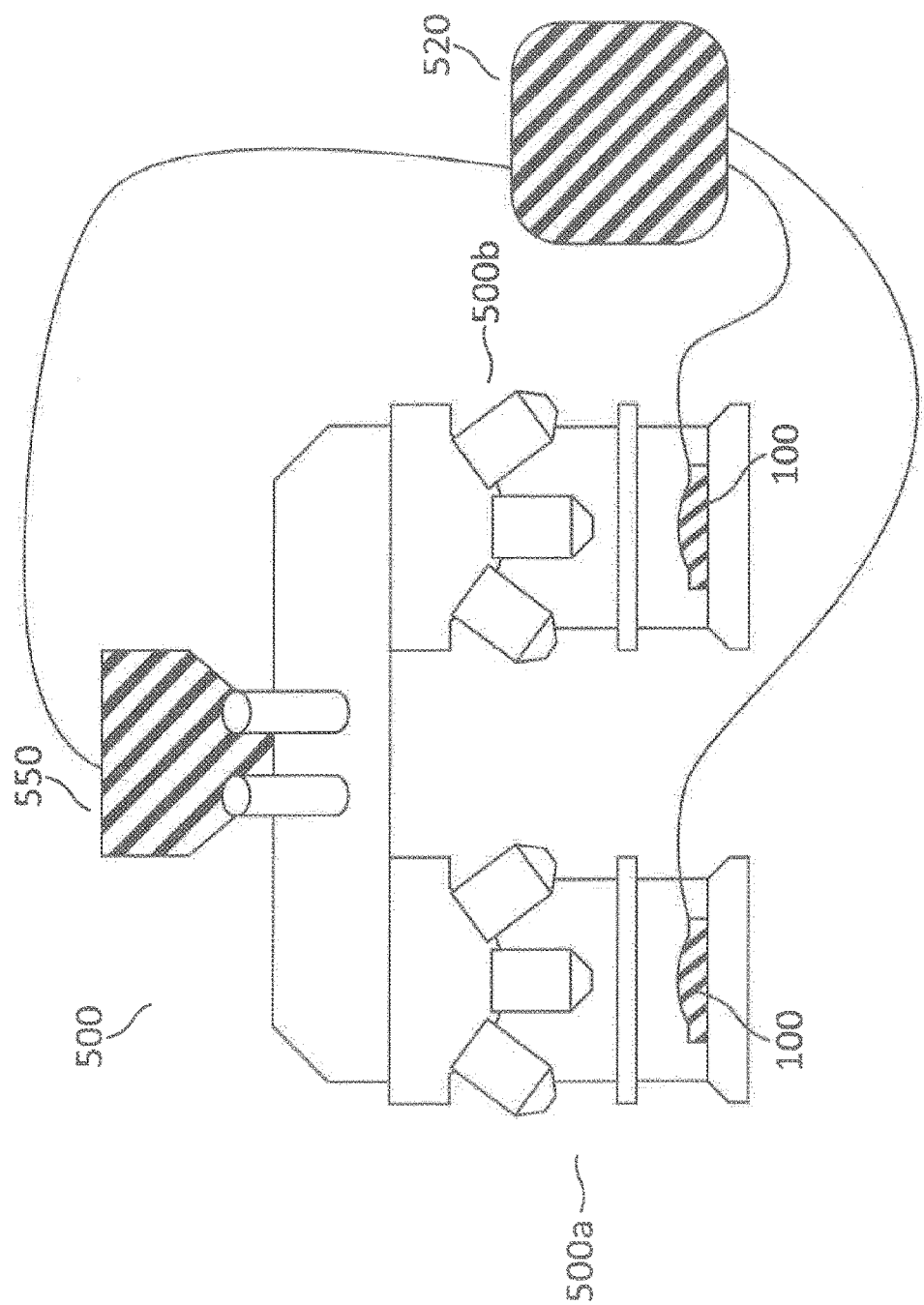
FIG. 5 is a schematic view of a second preferred embodiment of a comparison microscope embodied with an illumination device according to the present invention.

A further preferred embodiment of a microscope that is embodied with an illumination device according to the present invention is depicted in FIG. 5 and labeled 500 in its entirety. Microscope 500 is once again embodied as a comparison microscope having two sub-microscopes 500a, 500b.

Comparison microscope 500 differs from comparison microscope 300 depicted with reference to FIG. 3 only in that a digital camera 550 is provided, with which an automatic color compensation of the frequency spectra or illumination impressions of illumination devices 100 according to the present invention can be carried out. Here as well, an automated color compensation of the two image channels of sub-microscopes 500a, 500b can be accomplished using control unit 520.

The invention presented can be integrated into both upright and inverted microscopes, and into the illumination base of stereomicroscopes and stereomacroscopes. It is suitable equally for transmitted and incident illumination systems. As already indicated, arrangement of the at least one transparent or semitransparent self-luminous layer (in particular, OLED layer) in or near the aperture plane is possible; it is likewise conceivable to provide the layers in other suitable planes of an existing conventional illumination system. These planes can be of flat or spherical configuration, for example in the form of a conical section or a free-form surface. It is possible in particular to use available surfaces of an existing illumination system, for example of a lens or diffusion disk, as substrates onto which the layers can be applied, for example vapor-deposited. It is possible, for example, to introduce into plane 101 a transparent substrate onto which various OLED layers or TOLED layers can be applied. It is likewise conceivable to apply these layers, for example, onto lens 102 and/or onto lens 105.

Figure 6:
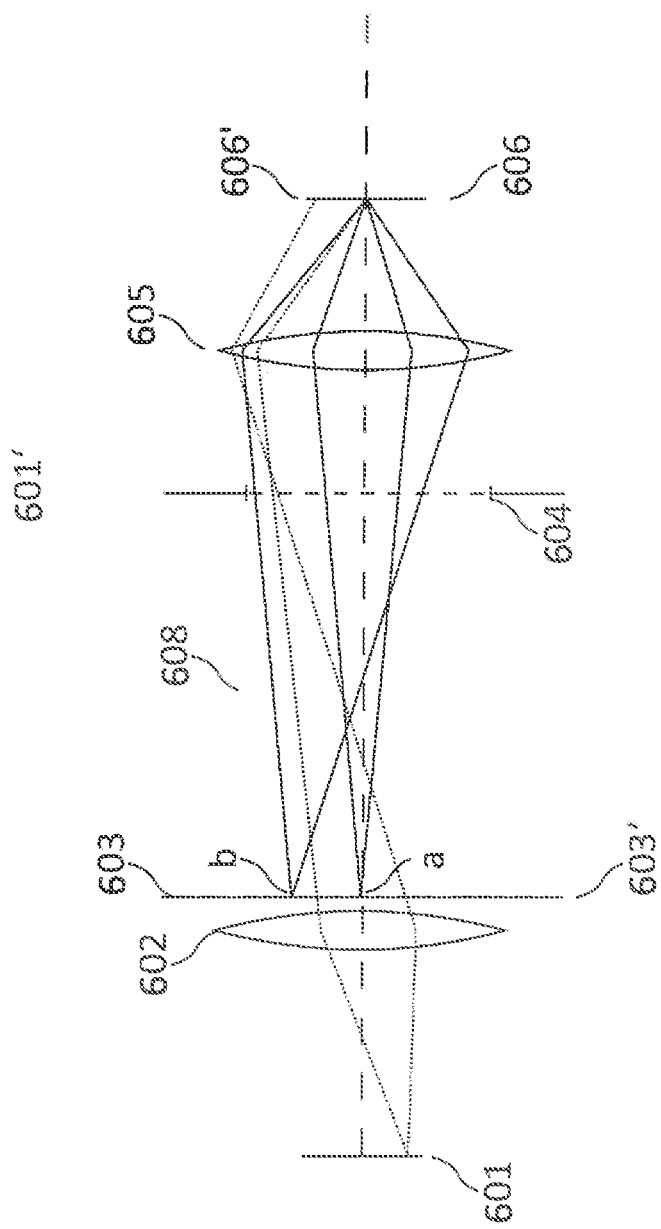
FIG. 6 is a schematic side view of a second preferred embodiment of an illumination device according to the present invention.

The preferred embodiment depicted in FIG. 6 of an illumination device having an apparatus for inhomogeneity compensation is labeled 600 in its entirety and serves for illumination of an object 606. The illumination device can be embodied, for example, for a microscope or macroscope.

Illumination device 600 comprises a light source 601, for example in the form of an incandescent lamp or LED, the light of which is guided via a system of lenses 602, 605 along an illumination beam path 608 in order to illuminate object 606 that is to be investigated. The surface of object 606 is arranged in an object plane 606'.

Lens 602 is embodied as a collector lens, and lens 605 as a condenser lens. It is of course possible to provide, at the positions of these lenses, collector or condenser optical systems each encompassing multiple lenses.

An aperture diaphragm 604, by means of which the illumination light intensity is adjustable, is embodied in a plane 601' conjugated with the plane of light source 601.

At least one semitransparent, self-luminous layer 603, which preferably is embodied as an OLED or TOLED, is introduced into illumination beam path 608 in an intermediate image plane 603' or close to said plane.

The at least one layer 603 is embodied in planarly patterned fashion, so that different regions of layer 603 can be embodied with different illumination intensities. This is possible, for example, by dividing layer 603 into different regions that are individually contacted and controllable (by means of a control device). It is possible, for example, to activate a first region of layer 603 more intensely (for example, with a higher voltage) than a second region, with the result that the first region emits light correspondingly more intensely than the second one. A corresponding electronic activation system (control unit) is embodied for correspondingly individual contacting and activation of these individual regions. Thanks to this selective activation, the illumination light from (main) light source 601 can have further light, selectively three-dimensionally patterned and having a corresponding brightness, mixed into it. The result of arranging the at least one layer 603 in the intermediate image plane is that the luminous pattern of self-luminous layer 603 is imaged onto object plane 606'. The transparency or semitransparency of the at least one layer 603 at the same time ensures transmission of the illumination light of (main) light source 601.

It is possible in particular to embody layer 603 as a single layer that makes available an additional white illumination light. OLEDs or TOLEDS of this kind that emit white light are commercially available.

Because of the shallow depth of field of microscope illumination systems, however, it is likewise possible to furnish an additional white illumination light by superimposing layers 603, in particular OLED layers or TOLED layers, that differ in terms of color. Layers of this kind provided one above another can, for example, extend over an RGD (red-green-blue) color space. Usefully, the individually activatable regions of the respective layers are associated with one another, i.e. in particular each arranged above one another.

By means of this type of three-dimensional patterning of the at least one layer 603 it is possible in particular to compensate effectively for an inhomogeneous illumination, often occurring in conventional systems, of a field of view which decreases toward the edge of the field of view. The three-dimensional or planar patterning of the at least one layer can therefore be embodied, in particular, rotationally symmetrically around the optical axis of the illumination optical system.

According to further embodiments, however, it is also possible to provide a pattern made up of individual, for example quadrilateral, rectangular, or circular regions (pixels), or also a pattern segmented in another manner.

Arrangement of the at least one self-luminous layer in a plane other than intermediate image plane 603' is, however, also possible, In particular, the at least one self-luminous layer 603 can be applied, for example, onto one of lenses 602, 605, or a lens of the corresponding collector or condenser optical system.

Figure 7:
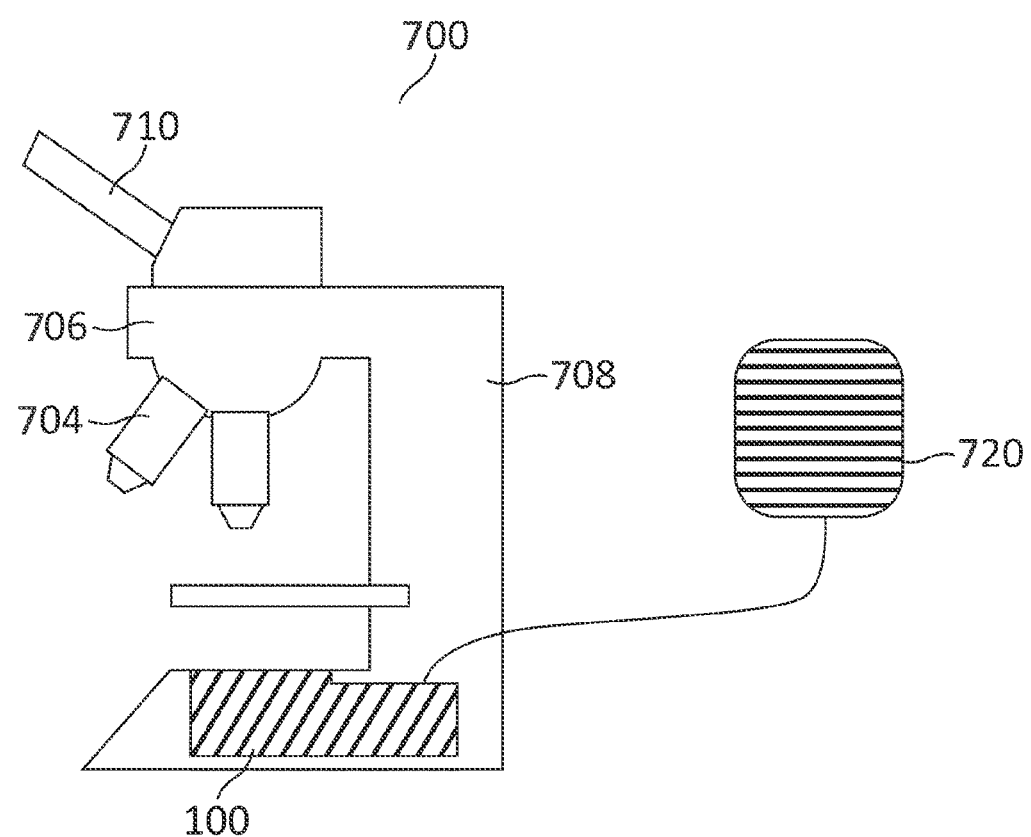
FIG. 7 is a schematic view of a further preferred embodiment of a microscope embodied with the second illumination device according to the present invention.

In FIG. 7 a first preferred embodiment of a microscope embodied with an illumination device according to the present invention is labeled 700 in its entirety. When a "microscope" is referred to hereinafter, i.e. with reference to FIGS. 7 to 9, the term "macroscope" is also always to be encompassed thereby as well. Microscope 700 is embodied with a transmitted illumination device 600 that comprises, for example, corresponding components 601, 602, 603, 604, 605 for transmitted illumination of an object positionable on a specimen slide 702. Further components of microscope 700 are likewise depicted merely schematically in FIG. 7. Multiple objectives or magnification optics 704 provided on an objective turret 706, a microscope housing 708, and an eyepiece 710 are, for example, apparent. Be it noted that the depiction of a microscope having transmitted illumination is merely exemplifying. The present invention is usable in the same manner in conjunction with incident illumination.

The brightness of the illumination light furnished by illumination device 700 is controllable by means of a control unit 720. If illumination device 600 encompasses, for example, a selectively activatable OLED layer or TOLED layer 603, as described above with reference to FIG. 6, individual regions of this OLED or TOLED are individually activatable so that light having a desired intensity can be blended into the illumination light of (main) light source 601 in the respective individually activatable regions of the field of view.

It is possible, for example by introduction of a reference sample (generally a transparent sample for transmitted-light arrangements as depicted in FIG. 7, typically a homogeneously diffusing surface for incident-light arrangements), for a user of the microscope to achieve a desired homogenization of the field illumination by suitably activating illumination device 600 by actuating control unit 720. The field of view can, for example, be suitably parameterized for this purpose, in which context a radial distribution by means of splines or via Zernike polynomials can in particular be used.

Figure 8:
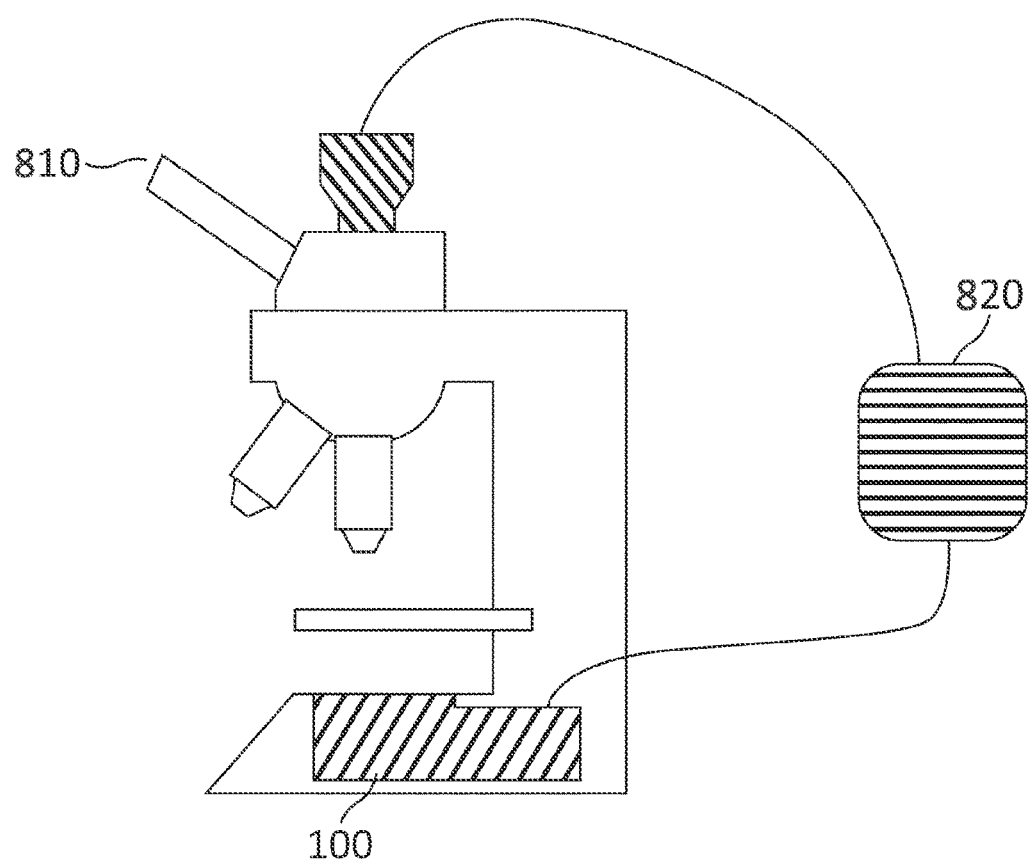
FIG. 8 is a schematic view of a further preferred embodiment of a microscope embodied with the second illumination device according to the present invention.

A further preferred embodiment of a microscope having an illumination device according to the present invention is depicted in FIG. 8 and labeled 800 in its entirety. The microscope depicted in FIG. 8 corresponds to the one depicted in FIG. 7, a digital camera 850 additionally being provided. It is possible by means of such a camera, using an illumination device 600 according to the present invention, to establish an automatic adjustment of the brightness of the illumination device. This brightness adjustment can be accomplished, for example, by means of the control unit here labeled 820, with the aid of an automatic algorithm. The latter can, for example, regulate detected brightness values of a reference sample to a previously defined target value.

Automated illumination homogenization can be implemented, for example, by acquiring the microscopic image using camera 850. By calculating the deviation in brightness of individual image regions, for example, from the maximum brightness of the image, it is possible to calculate in spatially resolved fashion the respective local brightness that is to be blended into respective regions using the self-luminous layer. The optimum configuration of this blending pattern which is calculated in this context is then made available by the selectively activatable layer 603, consideration possibly being given to imaging properties of the illumination optical system. This automatic illumination correction can be accomplished via a direct or an iterative method. The calculated illumination correction for the respective illumination situation (for example as a function of settings of light source 601 or of an objective being used) can be stored in a default setting for later reuse.

Figure 9:
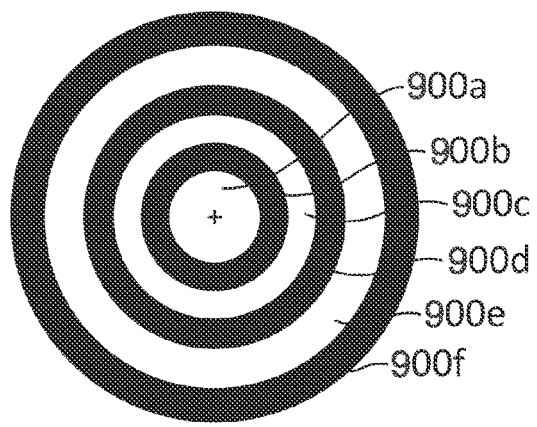
FIG. 9 shows various examples of possible patterns of the transparent or semitransparent self-luminous layers used according to embodiments of the present invention.
Figure 9:
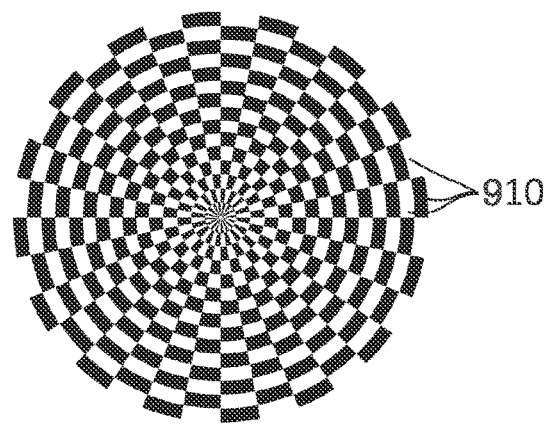
Figure 9:
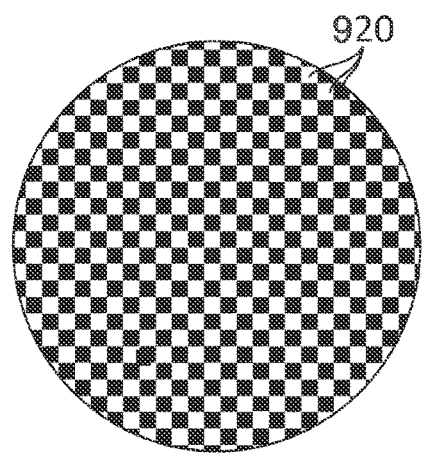

Various examples of spatial patterning of the at least one layer 603 (in particular OLED or TOLED) are depicted in FIG. 9.

In FIG. 9 at the top, a concentric ring pattern is implemented, the respective regions 900a to 900f being individually activatable. The depiction with dark and light regions is provided merely to illustrate the individually activatable annular regions and the circular center region.

In FIG. 9 in the middle, a further subdivision of these annular regions into individual regions or segments 910 is furnished. Even finer-scale adaptation to a desired homogeneity of the illuminated field can be furnished with selective activatability of the individual segments.

In FIG. 9 at the bottom, a further possible configuration capability for individually activatable regions of the at least one layer 603 is depicted, selectively activatable squares 920 here being provided in a Cartesian pattern.

The invention presented can be integrated into both upright and inverted microscopes, and into the illumination base of stereomicroscopes and stereomacroscopes. It is suitable equally for transmitted and incident illumination systems. As already indicated, arrangement of the at least one transparent or semitransparent self-luminous layer (in particular, OLED layer) in or near the intermediate image plane is possible; it is likewise conceivable to provide the layers in other suitable planes of an existing conventional illumination system. These planes can be of flat or spherical configuration, for example in the form of a conical section or a free-form surface. It is possible in particular to use available surfaces of an existing illumination system, for example of a lens or diffusion disk, as substrates onto which the layers can be applied, for example vapor-deposited. It is possible, for example, to introduce into intermediate image plane 601 a transparent substrate onto which various OLED layers or TOLED layers can be applied. It is likewise conceivable to apply these layers, for example, onto lens 602 and/or onto lens 605.

The illumination device according to the present invention can furthermore be integrated into the illumination base of a stereomicroscope or of a microscope, here preferably close to object plane 606'.

It is in particular also possible to place a diffusion disk after the at least one layer so that visibility of the patterns in the object plane can be avoided.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS

100 Illumination device
101 Light source
101' Conjugated plane (aperture plane)
102 Lens (collector lens)
103 Self-luminous layer
104 Aperture diaphragm
105 Lens (condenser lens)
106 Object
106' Object plane
108 Illumination beam path
200, 300, 400, 500 Microscope
202 Specimen slide
204 Objectives
206 Objective turret
208 Microscope housing
210 Eyepiece
220, 320, 420, 520 Control unit
300a, 300b Sub-microscopes
310 Eyepiece
312 Optical bridge
450, 550 Camera
500a, 500b Sub-microscopes
600 Illumination device
601 Light source
601' Conjugated plane (aperture plane)
602 Lens (collector lens)
603 Self-luminous layer
603' Intermediate image plane
604 Aperture diaphragm
605 Lens (condenser lens)
606 Object/object plane
606' Object plane
608 Illumination beam path
700, 800 Microscope
702 Specimen slide
704 Objectives
706 Objective turret
708 Microscope housing
710 Eyepiece
720, 820 Control unit
810 Eyepiece
850 Camera
900a-900f Regions of self-luminous layer
910 Regions (segments) of self-luminous layer
920 Regions (squares) of self-luminous layer

The invention claimed is:
1. An illumination device for an optical device, a microscope or a macroscope, the illumination device comprising:

a first illumination source configured to emit light which is directed via an illumination beam path onto an object to be illuminated that is arranged in an object plane; and at least one second illumination source, positionable in the illumination beam path of the first illumination source, that is transparent or semitransparent as well as self-luminous and is configured to allow light emitted from the first illumination source to pass through at least in part, the at least one second illumination source having a number of individually activatable regions for furnishing a position-dependent illumination correction, wherein the object plane having the object to be illuminated is configured to be illuminated both by the first and by the at least one second illumination source.

2. The illumination device according to claim 1, wherein the at least one second illumination source is a self-luminous layer.

3. The illumination device according to claim 1, wherein the at least one second illumination source is an electroluminescent layer.

4. The illumination device according to claim 1, wherein the at least one second illumination source includes an organic light-emitting diode (OLED) or a transparent organic light-emitting device (TOLED).

5. The illumination device according to claim 1, wherein the at least one second illumination source is disposed in an aperture plane or in an intermediate image plane of the illumination beam path, or in a vicinity of the aperture plane or in a vicinity of the intermediate image plane.

6. The illumination device according to claim 1, wherein the at least one second illumination source has a planar surface or a curved surface, the at least one second illumination source being applied in particular onto a surface of an optical element provided in the illumination beam path.

7. The illumination device according to claim 1, further comprising a device configured to individually electrically activate the individually activatable regions of the at least one self-luminous layer.

8. The illumination device according to claim 1, wherein the at least one second illumination source is configured to adapt a color temperature furnished by the first illumination source.

9. The illumination device according to claim 1, wherein the at least one second illumination source is configured to compensate for inhomogeneities in a brightness distribution furnished by first illumination source.

10. The illumination device according to claim 1, wherein the at least one second illumination source includes at least two individually activatable OLED or TOLED layers.

11. A microscope or macroscope having an illumination device, the illumination device comprising:

a first illumination source configured to emit light which is directed via an illumination beam path onto an object to be illuminated that is arranged in an object plane; and at least one second illumination source, positionable in the illumination beam path of the first illumination source, that is transparent or semitransparent as well as self-luminous and is configured to allow light emitted from the first illumination source to pass through at least in part, the at least one second illumination source having a number of individually activatable regions for furnishing a position-dependent illumination correction, wherein the object plane having the object to be illuminated is configured to be illuminated both by the first and by the at least one second illumination source.

12. The microscope or macroscope according to claim 11, wherein the microscope or macroscope is a comparison microscope having at least two sub-microscopes, at least one sub-microscope or all of the sub-microscopes having the illumination device.

* * * * *